(12) United States Patent
Spruce et al.

(10) Patent No.: US 10,935,531 B2
(45) Date of Patent: Mar. 2, 2021

(54) INTEGRATED SENSOR PACKAGES

(71) Applicant: Hamilton Sundstrand Corporation, Charlotte, NC (US)

(72) Inventors: Jana Spruce, Charlotte, NC (US); Benjamin D. Gardner, Colton, CA (US); Richard K. Trubey, Upland, CA (US)

(73) Assignee: Hamilton Sundstrand Corporation, Charlotte, NC (US)

( * ) Notice: Subject to any disclaimer, the term of this patent is extended or adjusted under 35 U.S.C. 154(b) by 163 days.

(21) Appl. No.: 16/159,294

(22) Filed: Oct. 12, 2018

(65) Prior Publication Data
US 2020/0116689 A1    Apr. 16, 2020

(51) Int. Cl.
*G01N 27/12* (2006.01)
*G01N 33/00* (2006.01)
*G08B 21/14* (2006.01)

(52) U.S. Cl.
CPC ......... *G01N 33/0031* (2013.01); *G01N 27/12* (2013.01); *G01N 33/0075* (2013.01); *G08B 21/14* (2013.01)

(58) Field of Classification Search
CPC combination set(s) only.
See application file for complete search history.

(56) References Cited

U.S. PATENT DOCUMENTS

| 7,171,312 B2 | 1/2007 | Steinthal et al. | |
|---|---|---|---|
| 2013/0092029 A1* | 4/2013 | Morgan | B01D 53/30 |
| | | | 96/111 |
| 2016/0282151 A1 | 9/2016 | Kursula et al. | |
| 2017/0023509 A1 | 1/2017 | Kim et al. | |
| 2018/0174423 A1* | 6/2018 | Trubey | G01N 33/0062 |
| 2018/0195987 A1 | 7/2018 | Hur et al. | |
| 2018/0220967 A1 | 8/2018 | Wang et al. | |
| 2019/0331582 A1* | 10/2019 | Mou | G01N 15/0637 |

FOREIGN PATENT DOCUMENTS

| WO | 2000/025108 A1 | 5/2000 |
|---|---|---|
| WO | 2016/145300 | 9/2016 |

OTHER PUBLICATIONS

Reza Goldoust et al., "Design and Implementation of a Preconcentrator with Zeolite NaY for Sensitivity Enhancement of Commercial Gas Sensors at Low NO 2 Concentrations", Materials Research Express, vol. 6, No. 1, Oct. 10, 2018.
Extended European Search Report dated Mar. 18, 2020, issued during the prosecution of European Patent Application No. EP 19203110.2.

* cited by examiner

*Primary Examiner* — Nguyen Q. Ha
(74) *Attorney, Agent, or Firm* — Locke Lord LLP

(57) ABSTRACT

A chemical detecting system includes a sensor module including a sensor configured to detect at least one chemical of a selected set of chemicals. A screen is operatively connected to protect the sensor from debris. The screen is configured to permit ambient gases therethrough for detection by the sensor. A controller module is stacked together with the sensor module and including a controller operatively connected to the sensor. A battery terminal is operatively connected to the controller, the battery terminal being configured to connect to a battery to power the controller and the sensor.

17 Claims, 4 Drawing Sheets

INTEGRATED SENSOR PACKAGES

BACKGROUND OF THE INVENTION

1. Field of the Invention

The present disclosure generally relates to chemical detection, and more particularly to chemical sensors.

2. Description of Related Art

Chemical threat detection generally relates to the recognition of and alert to any number of known toxic chemical vapors in the environmental background. Military and homeland security applications include the detection of chemical warfare agents and toxic industrial chemicals used by enemy states or terrorists to intentionally harm military troops or civilians abroad or in the U.S. Chemical munitions left behind from old conflicts routinely present a chemical hazard to the military. The ability to detect toxic chemicals is important in a variety of other contexts, including the detection of potentially toxic chemicals in a home, business, or factory to prevent fire, injury, death, or health problems. The early detection of chemical agents and toxic chemical vapors in general may provide an opportunity to warn military personnel or the public in sufficient time to provide an opportunity for appropriate evacuation, personal protection by donning protective equipment, or containment of the chemical threat source.

Typical chemical threat detectors are heavy and complex, thus making it difficult to transport and deploy multiple devices in large groups. Furthermore, typical costs for chemical threat detectors prohibit wide spread deployment to multiple users. Also, there is a tradeoff between achieving sensitive chemical detection and producing accurate chemical detection results that minimize false positive rates. The conventional techniques have been considered satisfactory for their intended purpose. However, there is an ever present need for an improved chemical threat detector. This disclosure provides a solution for this need.

SUMMARY OF THE INVENTION

A chemical detecting system (e.g. for detecting airborne chemicals) includes a sensor module including a sensor configured to detect at least one chemical of a selected set of chemicals. A screen is operatively connected to protect the sensor from debris. The screen is configured to permit ambient gases therethrough for detection by the sensor. A controller module is stacked together with the sensor module and including a controller operatively connected to the sensor. A battery terminal is operatively connected to the controller, the battery terminal being configured to connect to a battery to power the controller and the sensor.

A battery can be electrically connected to the battery terminal wherein the battery is not enclosed. The battery terminal can include a positive connector and a negative connector, wherein the positive connector and the negative connector are directed in a parallel direction so a single end of the battery can be electrically connected to the battery terminal for both positive charge and negative charge. The battery terminal can include a positive and negative connector facing each other so the battery can be connected at opposite ends of the battery to the battery terminal for both positive charge and negative charge.

A blower module can be stacked between the sensor module and the screen. The blower module can include a fan blower operatively connected to the controller for power and for controlling the blower to drive a flow of ambient gasses into the sensor. The blower module, sensor module, and controller module can be stacked one on top of another within a common foot print. The fan blower can be positioned to drive a stream of ambient gases directly onto the sensor along a single directional axis without intervening tubing or direction changes between the blower and the sensor.

The controller can include an application specific integrated circuit (ASIC) storing instructions that, when executed cause the system to electronically monitor the sensor for changes in resistance, or any other change, indicative of whether any of the at least one chemical of a selected set of chemicals is present within the environmental air sample. The instructions when executed can cause the system to determine information including at least one of a chemical name, a chemical concentration, a chemical category, or a toxicity level. The controller module can include a wireless connectivity module for wireless communication. The instructions when executed can cause the system to transmit the determined information from the wireless connectivity module to an external device.

The sensor module and controller module can be devoid of any display screen and/or graphical user interface for output. The instructions when executed can cause the system to activate a fan blower to acquire an environmental air sample into the sensor module.

The sensor can include an array of up to about 16 chemically tailored nanosensors. The array can be supported on a microelectromechanical system (MEMS) electrical resistance transducer platform. Each nanosensor can have a chemically-specific surface coating disposed thereon.

A system includes a closed loop circulating a gas therethrough and a chemical detecting system in fluid communication with gas flow through the closed loop. The chemical detecting system includes a sensor module including a sensor configured to detect at least one chemical of a selected set of chemicals and a controller module stacked together with the sensor module and including a controller operatively connected to the sensor. The closed loop can include a flow driver, and the chemical detecting system can be devoid of a blower in addition to the flow driver.

These and other features of the systems and methods of the subject disclosure will become more readily apparent to those skilled in the art from the following detailed description of the preferred embodiments taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, preferred embodiments thereof will be described in detail herein below with reference to certain figures, wherein.

DETAILED DESCRIPTION OF THE PREFERRED EMBODIMENTS

Figure 1:
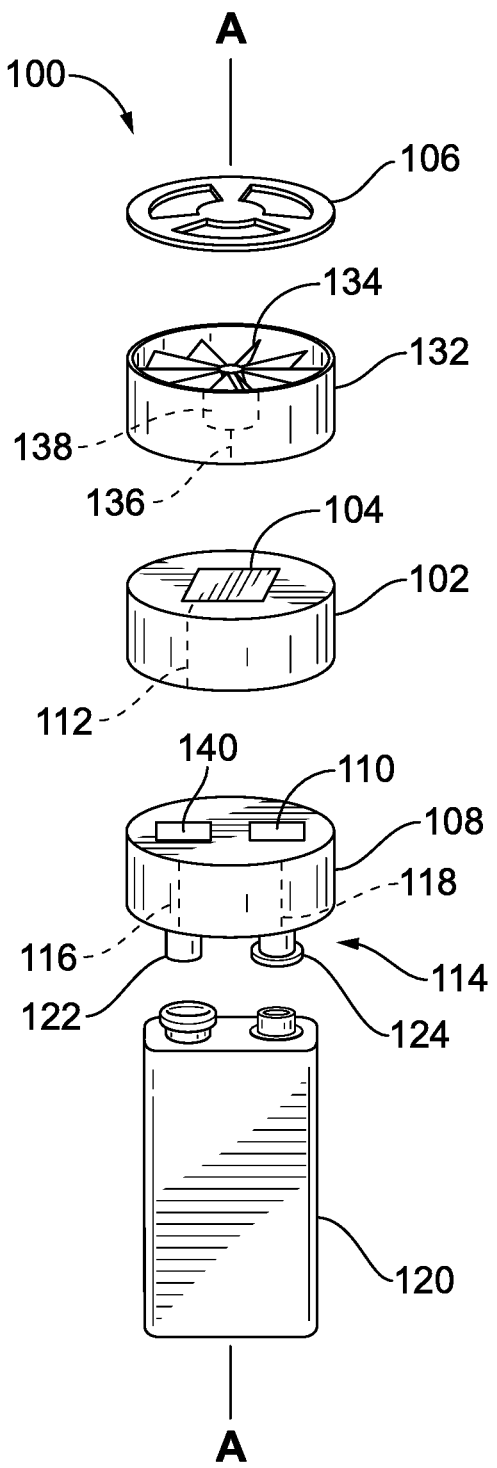
FIG. 1 is an exploded perspective view of an exemplary embodiment of a detecting system constructed in accordance with the present disclosure, showing the sensor module and the control module.

Reference will now be made to the drawings wherein like reference numerals identify similar structural features or aspects of the subject disclosure. For purposes of explanation and illustration, and not limitation, a partial view of an exemplary embodiment of a chemical detecting system in accordance with the disclosure is shown in FIG. 1 and is designated generally by reference character 100. Other embodiments of chemical detecting systems in accordance with the disclosure, or aspects thereof, are provided in FIGS. 2-4, as will be described. The systems and methods described herein can be used to reduce the size, weight, and complexity of portable chemical detection systems relative to traditional systems.

The chemical detecting system 100, e.g. a wearable system or detecting airborne chemicals, includes a sensor module 102 including a sensor 104 configured to detect at least one chemical of a selected set of chemicals. A screen 106 is operatively connected to protect the sensor 104 from debris. The screen 106 is configured to permit ambient gases therethrough for detection by the sensor 104. A controller module 108 is stacked together with the sensor module 102 and includes a controller 110 operatively connected to the sensor 104, e.g. through communication/power line 112. A battery terminal 114 is operatively connected to the controller through power lines 116, 118 to power the controller 110 and the sensor 104.

Figure 2:
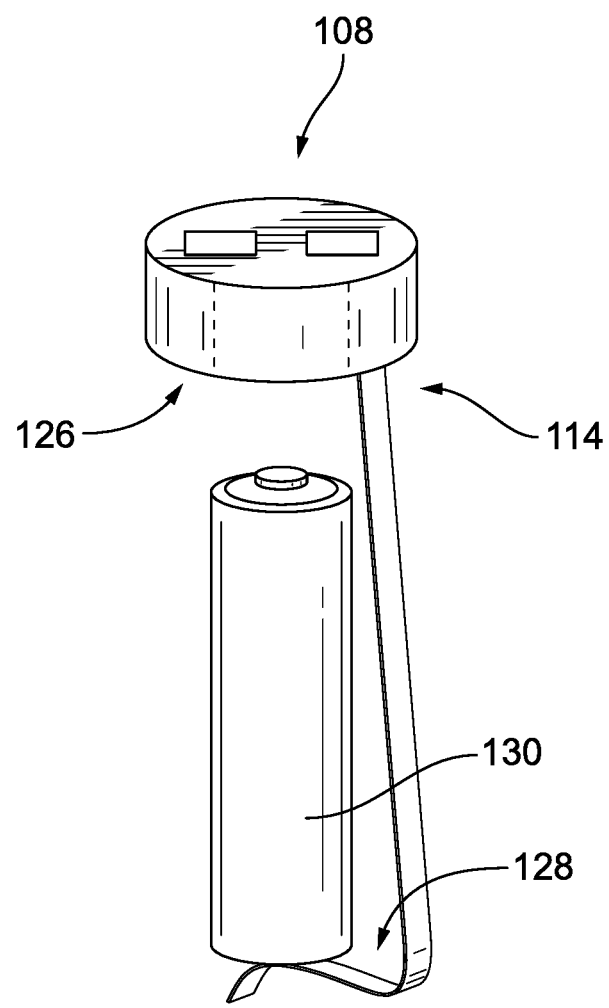
FIG. 2 is a perspective view of a portion of the system of FIG. 1, showing the control module with another type of battery terminal.

A battery 120 is electrically connected to the battery terminal 114 wherein the battery 120 is not enclosed in any kind of housing of the system 100. The battery terminal 114 includes a positive connector 122 and a negative connector 124, wherein the positive connector 122 and the negative connector 124 are directed in a parallel direction, i.e. the same direction, so a single end of the battery 114 is electrically connected to the battery terminal 114 for both positive charge and negative charge, e.g., as in the traditional 9V battery. As shown in FIG. 2, it is also contemplated that the battery terminal 114 can include a positive connector 126 and negative connector 128 facing each other so the battery 130 (e.g., a traditional 1.5V battery in this example) is connected at opposite ends of the battery 130 to the battery terminal 114 for both positive charge and negative charge. Even in the example of FIG. 2, the battery 130 is not enclosed in any housing of the system 100.

A blower module 132 is stacked between the sensor module 102 and the screen 106. The blower module 132 includes a fan blower 134 operatively connected by way of power/communication line 136 and motor 138 to the controller 110 for power and for controlling the blower 132 to drive a flow of ambient gasses into the sensor 104. The fan blower 134 is positioned to drive a stream of ambient gases directly onto the sensor 104 along a single directional axis A without intervening tubing or direction changes between the blower 134 and the sensor 104.

Figure 3:
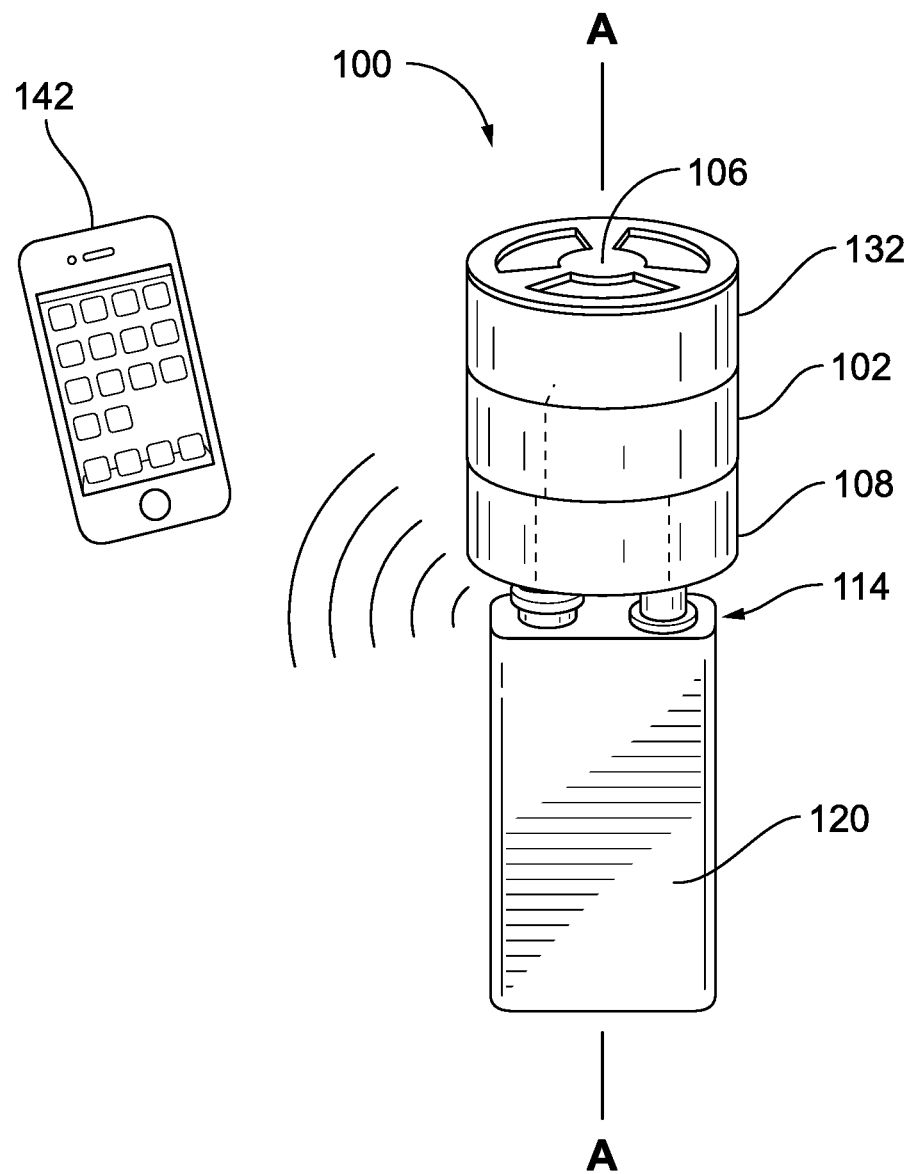
FIG. 3 is a perspective view of the system of FIG. 1, showing the common footprint of the modules, and schematically showing a wireless connection between the system and an external device.

With reference now to FIG. 3, the sensor module 102 and the controller module 108 are stacked one on top of another within a common foot print, which is shown as a circular footprint. However, those skilled in the art will readily appreciate that any other suitable footprint can be used without departing from the scope of this disclosure. The blower module 132 and screen 106 are also stacked within the common foot print. The blower module 132 can optionally be omitted for applications where the sensor 104 can sufficiently sample ambient gases without a forced flow.

The controller 110 includes an application specific integrated circuit (ASIC) storing instructions that, when executed cause the system 100 to electronically monitor the sensor 104 for changes in resistance indicative of whether any chemical in a selected set of chemicals is present within the environmental air sample. The instructions when executed can cause the system to activate the fan blower 134 to acquire an environmental air sample into the sensor module 102. The instructions when executed can cause the system 100 to determine information including at least one of a chemical name, a chemical concentration, a chemical category, or a toxicity level. The controller module 108 includes a wireless connectivity module 140 (identified in FIG. 1) for wireless communication with an external device such as a tablet or smart phone 142. The instructions when executed can cause the system 100 to transmit the determined information from the wireless connectivity module 140 to the external device 142, where information about chemicals detected with the sensor 104 can be displayed to a user. The sensor module 102, controller module 108 are devoid of any display screen and/or graphical user interface for output, which helps reduce the size of system 100 relative to traditional systems.

The sensor 104 can include an array of up to about 16 chemically tailored sensors. The array can be supported on a microelectromechanical system (MEMS) electrical resistance transducer platform. Each nanosensor can have a chemically-specific surface coating disposed thereon.

Figure 4:
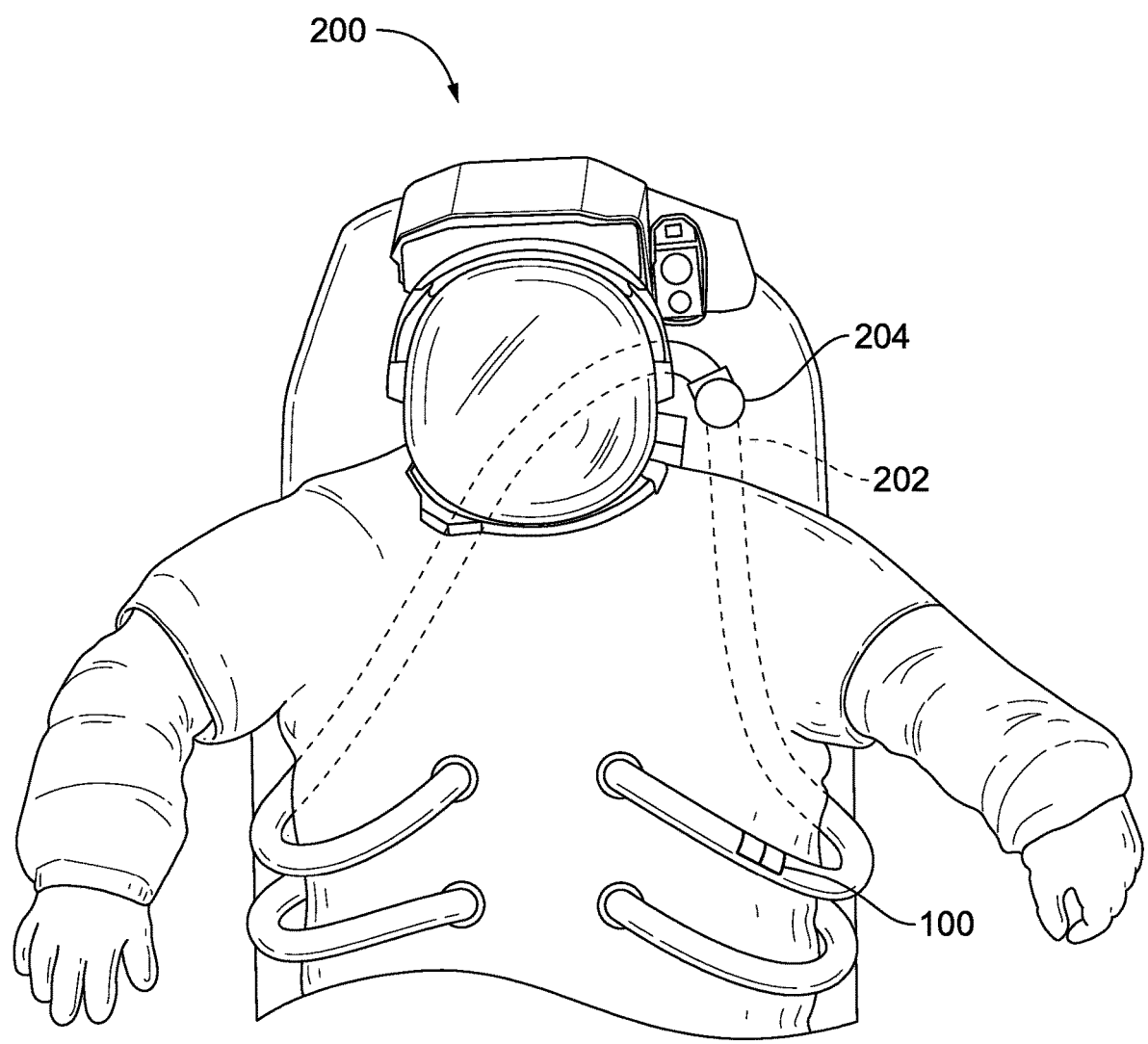
FIG. 4 is a schematic perspective view of a closed loop system, showing an chemical detecting system in the closed loop.

With reference now to FIG. 4, a system 200 such as a space suit, HAZMAT suit, diving suit, space vehicle, underwater vehicle, or the like, includes a closed loop 202 circulating a gas therethrough and a chemical detecting system 100 in fluid communication with gas flow through the closed loop 202. The chemical detecting system can be as described above, however, the fan blower 134 and/or screen 106 can be omitted because the closed loop 202 includes a flow driver, e.g., pump 204. The battery 120 can optionally also be omitted, e.g., if power is connected from the system 200 to power the chemical detecting system 100. The system 100 does not require any gas loss from the closed loop 202, unlike some traditional systems where a sample of gas has to be tapped off and removed from the closed loop for chemical sensing. Those skilled in the art will readily appreciate that system 200, although described above in the exemplary context of space, and the like can readily be used in suits or systems that are not air tight per se, without departing from the scope of this disclosure. Those skilled in the art will also readily appreciate that although described above in the exemplary context of closed loop systems, a system 200 can also be used in non-closed loop systems without departing from the scope of this disclosure.

The methods and systems of the present disclosure, as described above and shown in the drawings, provide for portable chemical detection with superior properties including reduced size, weight, and complexity relative to traditional systems. While the apparatus and methods of the subject disclosure have been shown and described with reference to preferred embodiments, those skilled in the art will readily appreciate that changes and/or modifications may be made thereto without departing from the scope of the subject disclosure.

What is claimed is:

1. A chemical detecting system, comprising:
a sensor module including a sensor configured to detect at least one chemical of a selected set of chemicals;
a screen operatively connected to protect the sensor from debris, wherein the screen is configured to permit ambient gases therethrough for detection by the sensor;
a controller module stacked together with the sensor module and including a controller operatively connected to the sensor;
a battery terminal operatively connected to the controller, the battery terminal being configured to electrically connect to a battery to power the controller and the sensor; and
a battery electrically connected to the battery terminal wherein the battery is not enclosed.

2. The system as recited in claim 1, wherein the battery terminal includes a positive connector and a negative connector, wherein the positive connector and the negative connector are directed in a parallel direction so a single end of the battery is electrically connected to the battery terminal for both positive charge and negative charge.

3. The system as recited in claim 1, wherein the battery terminal includes a positive and negative connector facing each other so the battery can be connected at opposite ends of the battery to the battery terminal for both positive charge and negative charge.

4. The system as recited in claim 1, wherein the sensor module and controller module are stacked one on top of another within a common foot print.

5. The system as recited in claim 1, further comprising a blower module stacked between the sensor module and the screen, wherein the blower module includes a fan blower operatively connected to the controller for power and for controlling the blower to drive a flow of ambient gasses into the sensor.

6. The system as recited in claim 5, wherein the blower module, sensor module, and controller module are stacked one on top of another within a common foot print.

7. The system as recited in claim 5, wherein the fan blower is positioned to drive a stream of ambient gases directly onto the sensor along a single directional axis without intervening tubing or direction changes between the blower and the sensor.

8. The system as recited in claim 1, wherein the controller includes an application specific integrated circuit (ASIC) storing instructions that, when executed cause the system to electronically monitor the sensor for changes in resistance indicative of whether any of the at least one chemical of a selected set of chemicals is present within the environmental air sample.

9. The system as recited in claim 8, wherein the instructions when executed cause the system to determine information including at least one of a chemical name, a chemical concentration, a chemical category, or a toxicity level.

10. The system as recited in claim 9, wherein the controller module includes a wireless connectivity module for wireless communication, and wherein the instructions when executed cause the system to transmit the determined information from the wireless connectivity module to an external device.

11. The system as recited in claim 10, wherein the sensor module and controller module are devoid of any display screen and/or graphical user interface for output.

12. The system as recited in claim 8, the instructions when executed cause the system to activate a fan blower to acquire an environmental air sample into the sensor module.

13. The system of claim 12, wherein the sensor includes an array of up to about 16 chemically tailored nanosensors.

14. The system of claim 13, wherein the array is supported on a microelectromechanical system (MEMS) electrical resistance transducer platform.

15. The system of claim 13, wherein each nanosensor has a chemically-specific surface coating disposed thereon.

16. A system comprising:
a closed loop circulating a gas therethrough; and a chemical detecting system in fluid communication with gas flow through the closed loop, wherein the chemical detecting system includes:
a sensor module including a sensor configured to detect at least one chemical of a selected set of chemicals;
a controller module stacked together with the sensor module and including a controller operatively connected to the sensor; and
a battery terminal operatively connected to the controller, the battery terminal being configured to electrically connect to a battery to power the controller and the sensor, wherein the battery is not enclosed.

17. The system as recited in claim 16, wherein the closed loop includes a flow driver, and wherein the chemical detecting system is devoid of a blower in addition to the flow driver.

* * * * *